US012806168B2

(12) United States Patent
Dhurandhar et al.

(10) Patent No.: US 12,806,168 B2
(45) Date of Patent: Nov. 24, 2026

(54) SMALL MOLECULE ANALOGS OF THE PROTEIN E4ORF1 IN THE TREATMENT AND PREVENTION OF METABOLIC DISORDERS

(71) Applicant: Texas Tech University System, Lubbock, TX (US)

(72) Inventors: Nikhil V. Dhurandhar, Lubbock, TX (US); Bhaskar C. Das, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 1038 days.

(21) Appl. No.: 17/421,671

(22) PCT Filed: Jan. 8, 2020

(86) PCT No.: PCT/US2020/012663
§ 371 (c)(1),
(2) Date: Jul. 8, 2021

(87) PCT Pub. No.: WO2020/146449
PCT Pub. Date: Jul. 16, 2020

(65) Prior Publication Data

US 2022/0071953 A1 Mar. 10, 2022

Related U.S. Application Data

(60) Provisional application No. 62/789,674, filed on Jan. 8, 2019.

(51) Int. Cl.
*A61K 31/37* (2006.01)
*A61K 31/15* (2006.01)
(Continued)

(52) U.S. Cl.
CPC .............. *A61K 31/37* (2013.01); *A61K 31/15* (2013.01); *A61K 31/4704* (2013.01); *A61K 31/69* (2013.01); *A61P 3/10* (2018.01)

(58) Field of Classification Search
CPC ........... A61P 3/10; A61K 31/37; A61K 31/15; A61K 31/4704; A61K 31/69
See application file for complete search history.

(56) References Cited

U.S. PATENT DOCUMENTS 8,008,436 B2 8/2011 Dhurandhar
8,338,401 B2 12/2012 Xu
(Continued)

FOREIGN PATENT DOCUMENTS

CN 108069929 5/2018
WO WO 2002/026713 4/2002
(Continued)

OTHER PUBLICATIONS

Pari et al. Chemico-Biological Interactions 181 (2009) 292-296 (Year: 2009).*
(Continued)

*Primary Examiner* — Kortney L. Klinkel
*Assistant Examiner* — Richard Grant Peckham
(74) *Attorney, Agent, or Firm* — Farhang Amini; Shackelford, McKinley & Norton, LLP

(57) ABSTRACT

In an embodiment, the present disclosure pertains to compositions and methods for modulating cellular glucose uptake. In general, the methods include associating cells with the compositions of the present disclosure. In another aspect, the present disclosure pertains to compositions and methods to treat or prevent a disorder in a subject. The methods generally include administering the compositions of the present disclosure to the subject.

10 Claims, 6 Drawing Sheets

Specification includes a Sequence Listing.

CHEMICAL FORMULA: $C_{11}H_7ClO_4$
MOLECULAR WEIGHT: 238.62
BT324

CHEMICAL FORMULA: $C_{10}H_5ClO_4$
MOLECULAR WEIGHT: 224.60
BT325

CHEMICAL FORMULA: $C_{11}H_8ClNO_3$
MOLECULAR WEIGHT: 237.64
BT326

CHEMICAL FORMULA: $C_{10}H_6ClNO_3$
MOLECULAR WEIGHT: 223.61
BT327

CHEMICAL FORMULA: $C_8H_9BrN_2O_2$
MOLECULAR WEIGHT: 245.08
BT328

CHEMICAL FORMULA: $C_9H_8N_2O$
MOLECULAR WEIGHT: 160.18
BT329

(51) Int. Cl.

| | |
|---|---|
| ***A61K 31/4704*** | (2006.01) |
| ***A61K 31/69*** | (2006.01) |
| ***A61P 3/10*** | (2006.01) |

(56) References Cited

U.S. PATENT DOCUMENTS

| | | | |
|---|---|---|---|
| 8,951,980 | B2 | 2/2015 | Dhurandhar |
| 9,346,835 | B2 | 5/2016 | Dhurandhar |
| 9,433,659 | B2 | 9/2016 | Dhurandhar |
| 9,469,659 | B2 | 10/2016 | Dhurandhar |
| 9,714,259 | B2 | 7/2017 | Dhurandhar |
| 10,047,107 | B2 | 8/2018 | Dhurandhar |
| 2012/0208829 | A1 | 8/2012 | Bakthavatchalam et al. |
| 2017/0037064 | A1 | 2/2017 | Dhurandhar |

FOREIGN PATENT DOCUMENTS

| | | | | |
|---|---|---|---|---|
| WO | WO-2006024545 A1 * | 3/2006 | | A61K 31/352 |
| WO | WO-2010037533 A1 * | 4/2010 | | C07D 215/54 |
| WO | WO 2013/101974 | 7/2013 | | |
| WO | WO2015164312 | 10/2015 | | |
| WO | WO-2015164312 A1 * | 10/2015 | | C07C 255/31 |
| WO | WO 2021/026495 | 2/2021 | | |

OTHER PUBLICATIONS

CDC ("About Type 1 Diabetes". Center for Disease Control. CDC.gov. 2024) (Year: 2024).*

Pari (Chemico-Biological Interactions 181 (2009) 292-296) (Year: 2009).*

Akbari (Inflammopharmacology (2018) 26:685-698) (Year: 2018).*

Extended Search Report for European Patent Application No. 20738769.7, mailed on Feb. 16, 2023.

Partial Search Report for European Patent App. No. 20738769.7, Mailed on Nov. 16, 2022.

Li Hanbing et al: "Coumarins as potential antidiabetic agents" Journal of Pharmacy and Pharmacology: JPP, vol. 69, No. 10, Jul. 3, 2017 (Jul. 3, 2017), pp. 1253-1264, XP05597594.

Dhurandhar, E.J., et al., E4orf1: a novel ligand that improves glucose disposal in cell culture. PLoS One, 2011. 6(8): p. e23394.

Dhurandhar, E.J., et al., E4orf1 improves lipid and glucose metabolism in hepatocytes: a template to improve steatosis & hyperglycemia. PLoS One, 2012. 7(10): p. e47813.

Krishnapuram, R., et al., Template to improve glycemic control without reducing adiposity or dietary fat. Am J Physiol Endocrinol Metab, 2011. 300(5): p. E779-89.

Na, H.N., et al., E4orf1 Enhances Glucose Uptake Independent of Proximal Insulin Signaling. PLoS One, 2016. 11(8): p. e0161275.

Shastri et al., E4orf1: A protein for enhancing glucose uptake despite impaired proximal insulin signaling, PLoS One, Dec. 6, 2018;13(12):e0208427.

International Search Report and the Written Opinion of the International Searching Authority for PCT/US 20/12663, Mailed on May 20, 2020.

Alabi et al. "Osthole activates glucose uptake but blocks full activation in L929 fibroblast cells, and inhibits uptake in HCLE cells", Life Sci. 2014. vol. 102(2}, pp. 105-110.

PubChem-CID-123277920, Create Date: Jan. 24, 2017 (Jan. 24, 2017).

PubChem-CID-11206360, Create Date: Oct. 26, 2006 (Oct. 26, 2006).

Office Action for Indian Pat. App. No. 202117035726, mailed on May 21, 2026.

Hegde et al., (2015). An adenovirus-derived protein: A novel candidate for anti-diabetic drug development. Biochimie, 121, 140-150. https://doi.org/10.1016/j.biochi.2015.12.002.

* cited by examiner

CHEMICAL FORMULA: $C_{11}H_7ClO_4$
MOLECULAR WEIGHT: 238.62
BT324

CHEMICAL FORMULA: $C_{10}H_5ClO_4$
MOLECULAR WEIGHT: 224.60
BT325

CHEMICAL FORMULA: $C_{11}H_8ClNO_3$
MOLECULAR WEIGHT: 237.64
BT326

CHEMICAL FORMULA: $C_{10}H_6ClNO_3$
MOLECULAR WEIGHT: 223.61
BT327

CHEMICAL FORMULA: $C_8H_9BrN_2O_2$
MOLECULAR WEIGHT: 245.08
BT328

CHEMICAL FORMULA: $C_9H_8N_2O$
MOLECULAR WEIGHT: 160.18
BT329

A + B → BN#3

A + B → BT#141

SEQUENCE LISTING

```
<160> NUMBER OF SEQ ID NOS: 1

<210> SEQ ID NO 1
<211> LENGTH: 125
<212> TYPE: PRT
<213> ORGANISM: Artificial Sequence
<220> FEATURE:
<223> OTHER INFORMATION: Ad36 E4orf1 Protein Translation

<400> SEQUENCE: 1

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
            20                  25                  30

Ser Phe His Ile Pro Pro His Gly Val Ile Leu Leu His Leu Arg Val
        35                  40                  45

Ser Val Leu Val Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
            100                 105                 110

Arg Val Ile Phe Pro Ser Val Arg Ile Ala Thr Leu Val
        115                 120                 125
```

SMALL MOLECULE ANALOGS OF THE PROTEIN E4ORF1 IN THE TREATMENT AND PREVENTION OF METABOLIC DISORDERS

CROSS-REFERENCE TO RELATED APPLICATIONS

This application claims priority to U.S. Provisional Patent Application No. 62/789,674, filed on Jan. 8, 2019. The entirety of the aforementioned application is incorporated herein by reference.

BACKGROUND

Early 4 open reading frame 1 protein of human adenovirus 36 (E4orf1) has been effective in glycemic control. However, without an effective delivery method, E4orf1 has limited abilities in treating human patients. For example, there is no receptor for E4orf1 in human cells, which makes it challenging to deliver the E4orf1 protein to humans. The present disclosure seeks to circumvent this limitation by using small molecule analogs of E4orf1 to modulate cellular glucose uptake.

SUMMARY

In some embodiments, the present disclosure pertains to a method of modulating cellular glucose uptake. The method can generally include associating cells with a composition. In some embodiments, the composition can include one or more of the following compounds:

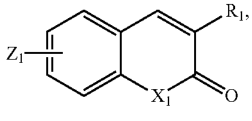

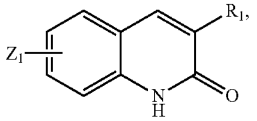

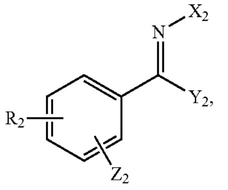

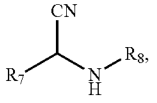

combinations thereof.

In some embodiments, the composition can include one or more of the following compounds:

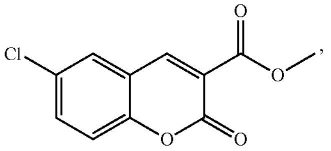

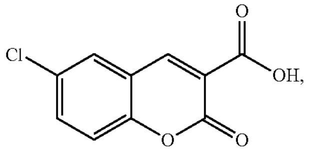

-continued

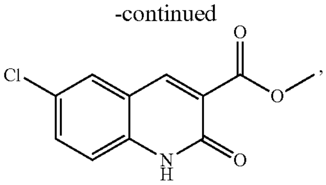

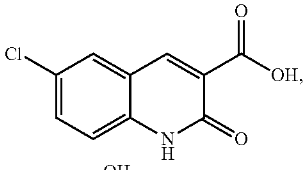

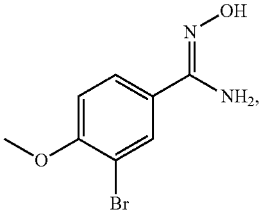

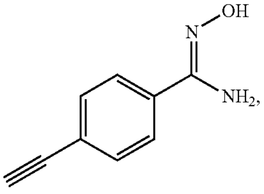

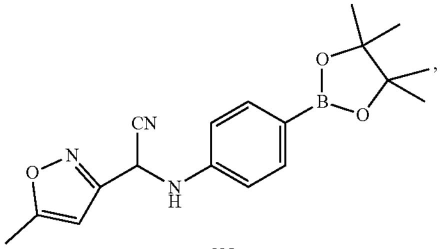

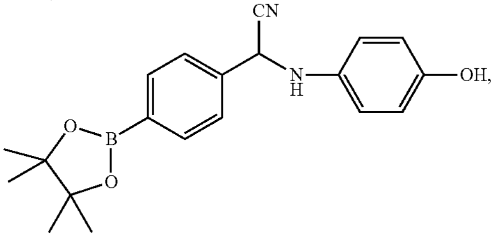

or combinations thereof.

In some embodiments, the association of the compositions of the present disclosure with cells is performed in vitro or in vivo in a subject. In some embodiments, the associating includes administering one or more of the compositions outlined above to the subject. In some embodiments, the administering is performed orally, intramuscularly, intranasally, subcutaneously, intra- or trans-dermally, intravenously, or through combinations of such methods.

In some embodiments, the aforementioned compositions are used to treat or prevent a disorder in a subject. In some embodiments, the disorder is prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steatohepatitis (NASH), liver dysfunction characterized by fatty liver and/or insulin resistance, polycystic ovary syndrome, or combinations thereof.

In some embodiments, the aforementioned compositions increase cellular glucose uptake. In some embodiments, the aforementioned compositions increase cellular glucose uptake in fat cells, muscle cells, or liver cells. In some embodiments, the aforementioned compositions increase cellular glucose uptake independently of proximal insulin signaling pathways. In some embodiments, the aforementioned compositions mimic function of early 4 open reading frame 1 protein of human adenovirus 36 (E4orf1). In some embodiments, the aforementioned compositions mimic function of E4orf1 in glucose uptake and insulin signaling in cells. In some embodiments, the aforementioned compositions cause an increase in pAkt/Akt in cells.

In some embodiments, the compositions of the present disclosure can reduce endogenous insulin levels in the blood. In some embodiments, the compositions of the present disclosure improve blood glucose levels by reducing high levels of glucose in the blood, or reducing the rise in glucose levels or the duration of glucose elevation expected after eating food. In some embodiments, the compositions of the present disclosure reduce glucose output from the liver. In some embodiments, the compositions of the present disclosure prevent an increase in blood insulin levels, reduce production and secretion of insulin while improving blood glucose levels, and thereby prevent damage to pancreatic cells that make insulin.

In some embodiments, the compositions of the present disclosure reduce fat accumulation in the liver. In some embodiments, the compositions of the present disclosure prevent accumulation of fat in the liver or reduce accumulated lipid from the liver.

In some embodiments, the compositions of the present disclosure are associated with delivery agents, such as nanoparticles. In some embodiments, the compositions of the present disclosure are associated with one or more solubilizing agents.

In some embodiments, the present disclosure pertains to a method of treating or preventing a disorder in a subject. The method can generally include administering one or more of the compositions of the present disclosure to the subject. In some embodiments, the disorder can include, without limitation, prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steato-hepatitis (NASH), liver dysfunction characterized by fatty liver and/or insulin resistance, polycystic ovary syndrome, or combinations thereof. In some embodiments, the administering can be performed orally, intramuscularly, intranasally, subcutaneously, intra- or trans-dermally, intravenously, or combinations thereof.

DETAILED DESCRIPTION

Figure 1:
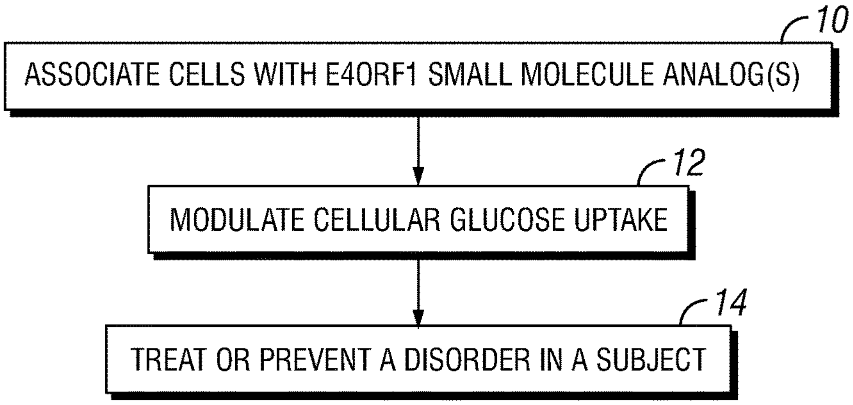
FIG. 1 illustrates a method of modulating cellular glucose uptake in cells.
Figure 2:
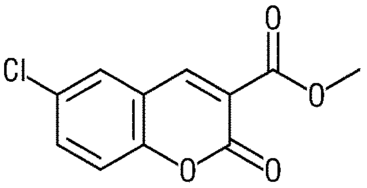
FIG. 2 depicts the structures of various active E4orf1 analogs.
Figure 2:
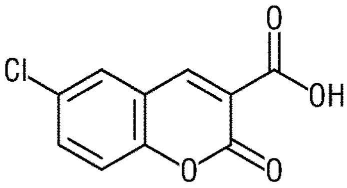
Figure 2:
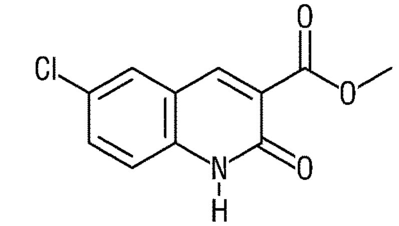
Figure 2:
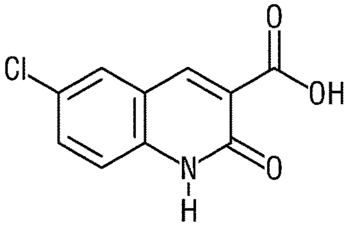
Figure 2:
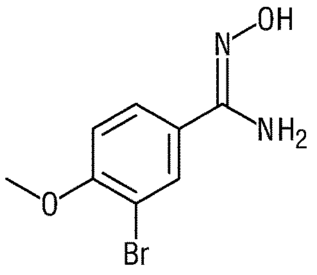
Figure 2:
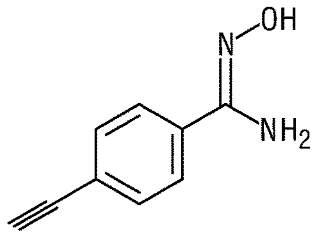

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

According to the National Institutes of Health, more than 1 in 3 adults are considered to have obesity. In addition, 1 in 6 children and adolescents ages 2 to 19 are considered to have obesity. The prevalence of obesity in the developed world is increasing. Becoming obese puts individuals at risk for several different health conditions, including hypertension, dyslipidemia, heart disease, stroke, and diabetes.

Applicants of the present disclosure have spent many years researching the mechanisms of obesity and diabetes. Applicants have discovered a virus that showed a strong correlation with the development of obesity in humans (referred to as infectobesity). The virus is part of the adenoviridae family and is known as human adenovirus 36. This virus was found within the fat cells of obese and diabetic humans and animals. When experimental animals such as mice or rats are infected with this virus, they improve glucose levels and reduce the requirement of endogenous insulin.

Applicants discovered that a protein made by human adenovirus 36, early 4 open reading frame 1 (E4orf1), seemed to decrease fat in the liver (leading to a cleaner liver), increase the uptake of glucose in fat and muscle cells (which lowers blood sugar levels), and lower the levels of endogenous insulin in animal models. These effects can be utilized to treat and prevent various metabolic disorders, including diabetes.

While E4orf1 has a lot of therapeutic potential, there are still challenges with its ability to treat human patients. In particular, there is no receptor for E4orf1 in human cells. As such, a need exists for more effective compositions and methods for maximizing the therapeutic potential of E4orf1. Various embodiments of the present disclosure address the aforementioned need.

In some embodiments, the present disclosure pertains to methods of modulating cellular glucose uptake. In some embodiments illustrated in FIG. 1, the methods of the present disclosure include a step of associating cells with one or more compositions that include one or more E4orf1 small molecule analogs (step 10). The association results in the modulation of cellular glucose uptake (step 12). In some embodiments where the association occurs in vivo in a subject, the method can be utilized to treat or prevent a disorder in the subject (step 14).

As set forth in more detail herein, the compositions and methods of the present disclosure can have numerous embodiments. For instance, the compositions of the present disclosure can include various E4orf1 small molecule analogs with various chemical configurations and moieties. Furthermore, various methods may be utilized to modulate cellular glucose uptake in order to treat or prevent various disorders in various subjects.

Compositions

The compositions of the present disclosure can include various E4orf1 small molecule analogs. For instance, in some embodiments, the compositions of the present disclosure can include:

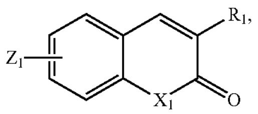
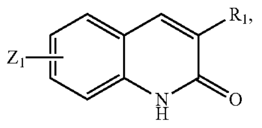
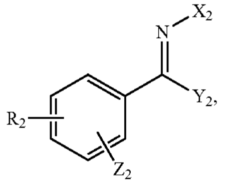
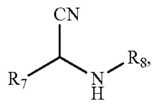

or combinations thereof.

In some embodiments, $R_1$ can be an alkyl group, an alkene group, an alkyne group, an alkoxyl group, an aldehyde, a carboxyl group, $COOR_3$, COOH, hydrogen, SH, SH derivatives, $SR_6$, or OH. In some embodiments, $R_3$ can be an alkyl group, an alkene group, an alkyne group, a methyl group, an ethyl group, a propyl group, a butyl group, or a pentyl group. In some embodiments, $R_6$ can be an alkyl group, an alkene group, an alkyne group, an alkoxyl group, an aldehyde, a carboxyl group, $COOR_3$, COOH, hydrogen, or OH.

In some embodiments, $Z_1$ and $Z_2$ each, independently, can be a halogen, hydrogen, SH, SH derivatives, an alkyl group, an alkene group, an alkyne group, or $SR_6$. In some embodiments, $X_1$ can be O, NH, $NR_4$, SH, SH derivatives, $CH_2$, $SR_6$, or S. In some embodiments, $R_4$ can be an alkyl group, an alkene group, an alkyne group, or a hydroxyl group. In some embodiments, $R_2$ can be $OR_5$, an alkyl group, an alkene group, an ethynyl group, an alkyne group, SH, SH derivatives, $SR_6$, or $COOR_5$. In some embodiments, $R_5$ can be hydrogen, an alkyl group, an alkene group, an alkyne group, a methyl group, an ethyl group, a propyl group, a butyl group, and a pentyl group. In some embodiments, $X_2$ and $Y_2$ each, independently, can be OH, $NH_2$, $NR_4$, an alkyl group, an alkene group, an alkyne group, a methyl group, an ethyl group, a propyl group, a butyl group, a pentyl group, SH, SH derivatives, or $SR_6$.

In some embodiments, $R_7$ and $R_8$ can each, independently, be

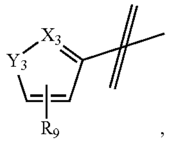
,
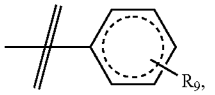

an alkyl group, an alkene group, an alkyne group, an alkoxyl group, an ethynyl group, an aldehyde, a carboxyl group, OH, $COOR_3$, COOH, hydrogen, SH, SH derivatives, $SR_6$, $OR_5$, or $COOR_5$. In some embodiments, $X_3$ can be N, CH, SH, SH derivatives, or P. In some embodiments, $Y_3$ can be O, NH, $NR_4$, SH, SH derivatives, $SR_6$, $CH_2$, or S. In some embodiments, $R_9$ can be an alkyl group, an alkene group, an alkyne group, an alkoxyl group, an ethynyl group, an aldehyde, a carboxyl group, $COOR_3$, COOH, hydrogen, SH, SH derivatives, $SR_6$, $OR_5$, $COOR_5$, $CH_3$, OH, or

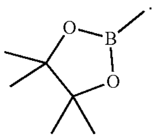

In some embodiments, $R_3$ can be alkyl group, an alkene group, an alkyne group, a methyl group, an ethyl group, a propyl group, a butyl group, or a pentyl group. In some embodiments, $R_5$ can be hydrogen, an alkyl group, an alkene group, an alkyne group, a methyl group, an ethyl group, a propyl group, a butyl group, and a pentyl group. In some embodiments, $R_6$ can be an alkyl group, an alkene group, an alkyne group, an alkoxyl group, an aldehyde, a carboxyl group, $COOR_3$, COOH, hydrogen, or OH.

In particular embodiments, the compositions of the present disclosure can include:

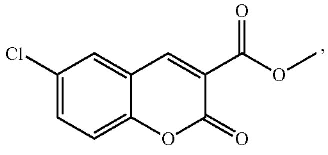
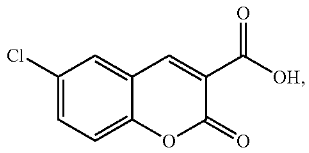
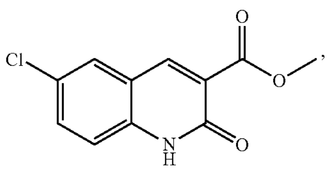

-continued

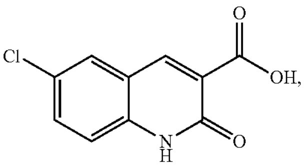,

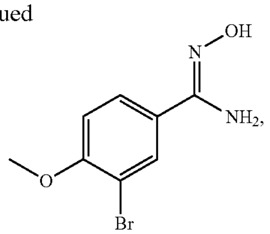,

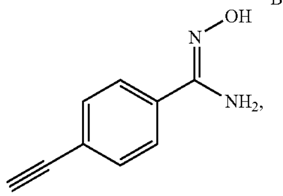,

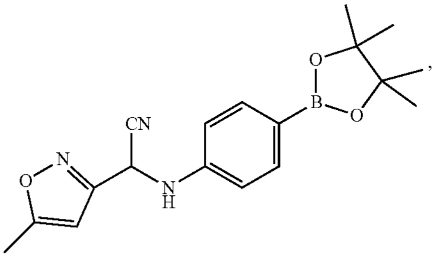,

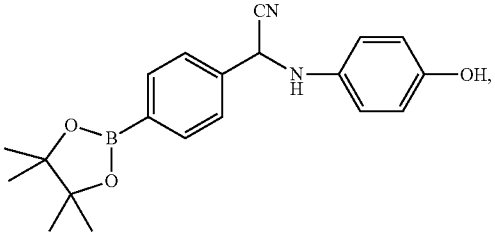, combinations thereof.

In some embodiments, the compositions of the present disclosure can include Compound 1, as shown herein.

Compound 1

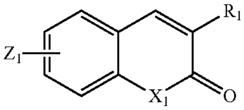

In some embodiments, Compound 1 can include various moieties in various configurations to make up Compound 1, including $R_1$, $X_1$, and $Z_1$. In some embodiments, $R_1$ can be an alkyl group, an alkene group, an alkyne group, an alkoxyl group, an aldehyde, a carboxyl group, $COOR_3$, COOH, hydrogen, SH, SH derivatives, $SR_6$, or OH. In some embodiments, $R_3$ can be an alkyl group, an alkene group, an alkyne group, a methyl group, an ethyl group, a propyl group, a butyl group, or a pentyl group.

In some embodiments, $Z_1$ can be a halogen, hydrogen, SH, SH derivatives, an alkyl group, an alkene group, an alkyne group, or $SR_6$. In some embodiments, $X_1$ can be O, NH, $NR_4$, SH, SH derivatives, $CH_2$, $SR_6$, or S. In some embodiments, $R_4$ can be an alkyl group, an alkene group, an alkyne group, or a hydroxyl group.

In some embodiments, $R_1$, $Z_1$, and $X_1$ can be SH, $SR_6$, SH derivatives, or combinations thereof. In some embodiments, $R_6$ can be an alkyl group, an alkene group, an alkyne group, an alkoxyl group, an aldehyde, a carboxyl group, $COOR_3$, COOH, hydrogen, or OH.

In a particular embodiment of Compound 1, $R_1$ is $COOCH_3$, $X_1$ is O, and $Z_1$ is Cl, as shown herein as compound BT324.

BT324

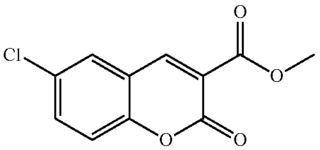

In a particular embodiment of Compound 1, $R_1$ is COOH, $X_1$ is O, and $Z_1$ is Cl, as shown herein as compound BT325.

BT325

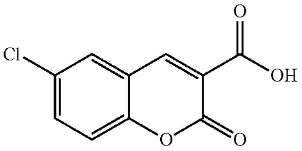

Moreover, in addition to Compound 1, as set forth in more detail herein, the compositions and methods of the present disclosure can include other configurations and/or moieties. For instance, in some embodiments, the compositions of the present disclosure can include a general configuration to that of Compound 2, as shown herein.

Compound 2

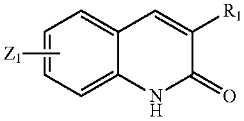

In some embodiments, Compound 2 can include various moieties in various configurations to make up Compound 2, and can include, but are not limited to, $R_1$ and $Z_1$.

In some embodiments, $R_1$ can be an alkyl group, an alkene group, an alkyne group, an alkoxyl group, an aldehyde, a carboxyl group, $COOR_3$, COOH, hydrogen, SH, SH derivatives, $SR_6$, or OH. In some embodiments, $R_3$ can be an alkyl group, an alkene group, an alkyne group, a methyl group, an ethyl group, a propyl group, a butyl group, or a pentyl group. In some embodiments, $Z_1$ can be a halogen, hydrogen, SH, SH derivatives, an alkyl group, an alkene group, an alkyne group, or $SR_6$.

In some embodiments, $R_1$ and $Z_1$, can be SH, $SR_6$, SH derivatives, or combinations thereof. In some embodiments, $R_6$ can be an alkyl group, an alkene group, an alkyne group, an alkoxyl group, an aldehyde, a carboxyl group, $COOR_3$, COOH, hydrogen, or OH.

In a particular embodiment of Compound 2, $R_1$ is $COOCH_3$ and $Z_1$ is Cl, as shown herein as compound BT326.

BT326

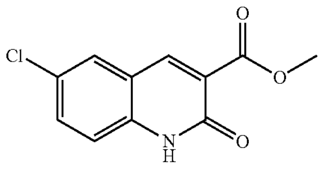

In a particular embodiment of Compound 2, $R_1$ is COOH and $Z_1$ is Cl, as shown herein as compound BT327.

BT327

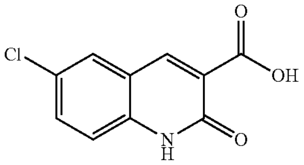

Furthermore, in addition to Compound 1 and Compound 2, as set forth in more detail herein, the compositions and methods of the present disclosure can include various different configurations and/or different moieties. In some embodiments, the compositions of the present disclosure can include Compound 3, as shown herein.

Compound 3

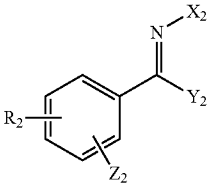

In some embodiments, Compound 3 can include various moieties in various configurations to make up Compound 3, and can include, but are not limited to, $R_2$, $X_2$, $Y_2$, and $Z_2$. In some embodiments, $R_2$ can be $OR_5$, an alkyl group, an alkene group, an ethynyl group, an alkyne group, SH, SH derivatives, $SR_6$, or $COOR_5$. In some embodiments, $R_5$ can be hydrogen, an alkyl group, an alkene group, an alkyne group, a methyl group, an ethyl group, a propyl group, a butyl group, and a pentyl group. In some embodiments, $Z_2$ can be a halogen, hydrogen, SH, SH derivatives, an alkyl group, an alkene group, an alkyne group, or $SR_6$.

In some embodiments, $X_2$ and $Y_2$ each, independently, can be OH, $NH_2$, $NR_4$, an alkyl group, an alkene group, an alkyne group, a methyl group, an ethyl group, a propyl group, a butyl group, a pentyl group, SH, SH derivatives, or $SR_6$. In some embodiments, $R_4$ can be an alkyl group, an alkene group, an alkyne group, or a hydroxyl group.

In some embodiments, $R_2$, $X_2$, $Y_2$, and $Z_2$ and can be SH, $SR_6$, SH derivatives, or combinations thereof. In some embodiments, $R_6$ can be an alkyl group, an alkene group, an alkyne group, an alkoxyl group, an aldehyde, a carboxyl group, $COOR_3$, COOH, hydrogen, or OH.

In a particular embodiment of Compound 3, $R_2$ is $OCH_3$, $Z_2$ is Br, $X_2$ is OH, and $Y_2$ is $NH_2$, as shown herein as compound BT328.

BT328

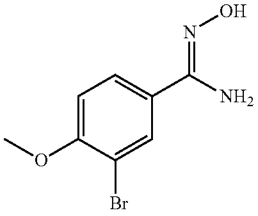

In a particular embodiment of Compound 3, $R_2$ is ethynyl (CCH), $Z_2$ is hydrogen, $X_2$ is OH, and $Y_2$ is $NH_2$, as shown herein as compound BT329.

BT329

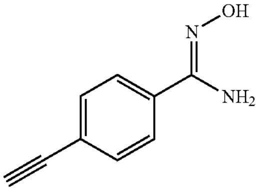

Moreover, in addition to the compounds outlined above, as set forth in more detail herein, the compositions and methods of the present disclosure can include further different configurations and/or different moieties. In some embodiments, the compositions of the present disclosure can include Compound 4, as shown herein.

Compound 4

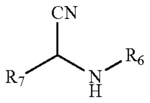

In some embodiments, Compound 4 can include various moieties in various configurations to make up Compound 4, and can include, but are not limited to, $R_7$ and $R_8$. In some embodiments, $R_7$ and $R_8$ each, independently, can be

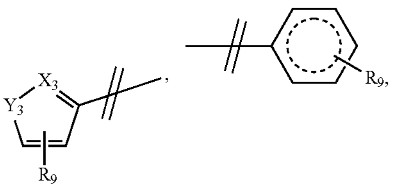

an alkyl group, an alkene group, an alkyne group, an alkoxyl group, an ethynyl group, an aldehyde, a carboxyl group, OH, $COOR_3$, COOH, hydrogen, SH, SH derivatives, $SR_6$, $OR_5$, or $COOR_5$. In some embodiments, $R_3$ can be an alkyl group, an alkene group, an alkyne group, a methyl group, an ethyl group, a propyl group, a butyl group, or a pentyl group. In some embodiments, $R_5$ can be hydrogen, an alkyl group, an alkene group, an alkyne group, a methyl group, an ethyl group, a propyl group, a butyl group, and a pentyl group. In some embodiments, $R_6$ can be an alkyl group, an alkene group, an alkyne group, an alkoxyl group, an aldehyde, a carboxyl group, $COOR_3$, COOH, hydrogen, or OH.

In some embodiments, $X_3$ can be N, CH, SH, SH derivatives, or P. In some embodiments, $Y_3$ can be O, NH, $NR_4$, SH, SH derivatives, $SR_6$, $CH_2$, or S. In some embodiments, $R_4$ can be an alkyl group or a hydroxyl group.

In some embodiments, $R_9$ can be an alkyl group, an alkene group, an alkyne group, an alkoxyl group, an ethynyl group, an aldehyde, a carboxyl group $COOR_3$, COOH, hydrogen, SH, SH derivatives, $SR_6$, $OR_5$, $COOR_5$, $CH_3$, OH,

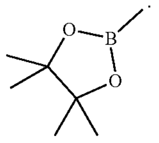

In a particular embodiment of Compound 4, $R_7$ is

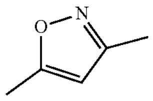

and $R_8$ is

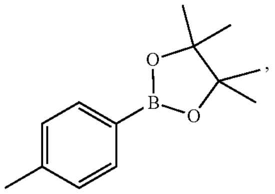

as shown herein as compound BN #3.

BN#3

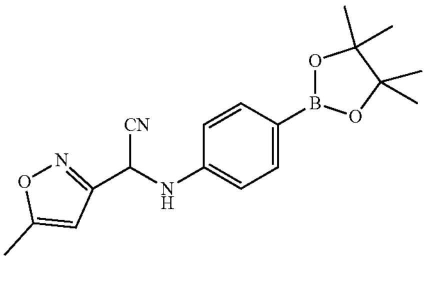

In a particular embodiment of Compound 4, $R_7$ is

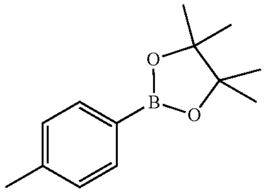

and $R_8$ is

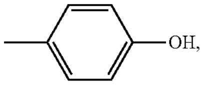

as shown herein as compound BT #141.

BT#141

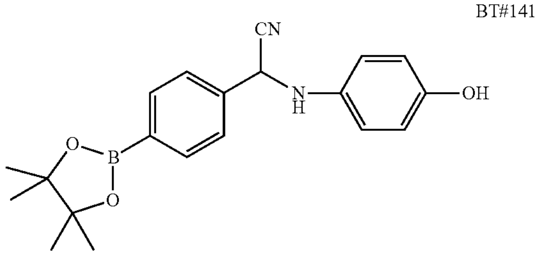 [SMILES: CC1(C)OB(c2ccc(C(C#N)Nc3ccc(O)cc3)cc2)OC1(C)C]

In some embodiments, the compositions of the present disclosure can contain one or more of the aforementioned compounds. In some embodiments, the compositions of the present disclosure can also have one or more physiologically acceptable carriers or excipients.

In some embodiments, the compositions of the present disclosure can also include formulation materials for modifying, maintaining, or preserving various conditions, including pH, osmolarity, viscosity, clarity, color, isotonicity, odor, sterility, stability, rate of dissolution or release, and/or adsorption or penetration of the compounds. Suitable formulation materials include, but are not limited to: amino acids (e.g., glycine); antimicrobials; antioxidants (e.g., ascorbic acid); buffers (e.g., Tris-HCl); bulking agents (e.g., mannitol and glycine); chelating agents (e.g., EDTA); complexing agents (e.g., hydroxypropyl-beta-cyclodextrin); and the like.

Association of Compositions with Cells

The compositions of the present disclosure may become associated with cells in various manners. For instance, in some embodiments, the compositions of the present disclosure become associated with cells by exposing the cells to the compositions. In some embodiments, the compositions of the present disclosure become associated with cells by incubating the cells with the compositions. In some embodiments, the compositions of the present disclosure become associated with cells by contacting the cells with the compositions.

In some embodiments, the cells can be fat cells, muscle cells, and/or liver cells. In some embodiments, the compositions of the present disclosure become associated with cells in vitro. In some embodiments, the compositions of the present disclosure become associated with cells in vivo in a subject, for example, a human or mammal. In some embodiments, the compositions of the present disclosure become associated with cells in vivo in a subject by administering the compositions to the subject.

Various methods may be utilized to administer the compositions of the present disclosure to a subject. For instance, in some embodiments, the administration occurs by a method that includes, without limitation, oral administration, inhalation, subcutaneous administration, intravenous administration, intra-nasal administration, intra-dermal administration, trans-dermal administration, intraperitoneal administration, intramuscular administration, intrathecal injection, topical administration, central administration, peripheral administration, and combinations thereof.

In some embodiments, the compositions of the present disclosure can be associated with cells via delivery agents. In some embodiments, the delivery agents can include various types of particles and/or targeting agents associated with the compositions of the present disclosure. For instance, in some embodiments, the delivery agents can be particles associated with the compositions of the present disclosure.

The particles associated with the compositions of the present disclosure may have various sizes. For instance, in some embodiments, the particles associated with the compositions of the present disclosure are in the form of nanoparticles. In some embodiments, the nanoparticles have diameters ranging from about 50 nm to about 500 nm. In some embodiments, the nanoparticles have diameters of about 100 nm to about 150 nm. In some embodiments, the nanoparticles can be, for example, polymeric nanoparticles, lipid-based nanoparticles, single wall or multiwall carbon nanotubes, fullerenes, and combinations thereof.

Targeting agents may be associated with the compositions of the present disclosure in various manners. For instance, in some embodiments, the targeting agents associated with the compositions of the present disclosure may be on a surface of a particle. In some embodiments, the targeting agents associated with the compositions of the present disclosure may be covalently linked to the surface of the particle. In some embodiments, the targeting agents associated with the compositions of the present disclosure may be linked to the surface of the particle through a linker, such as polyethylene glycol (PEG).

In some embodiments, the compositions of the present disclosure include a solubilizing agent. Solubilizing agents generally refer to one or more compounds that are capable of facilitating the solubilization of the compositions of the present disclosure in liquid formulations. Solubilizing agents may also be referred to as co-solvents or carriers.

In some embodiments, the solubilizing agents of the present disclosure include water miscible organic solvents. In some embodiments, the solubilizing agents of the present disclosure include, without limitation, polyethylene glycol (e.g., PEG 400 and/or PEG 300), glycerin, propylene glycol, ethanol, sorbitol, polyoxyethylated glycerides (e.g., Labrafil M-2125CS), polyoxyethylated oleic glycerides (e.g., Labrafil M-1944CS, Polyoxyl 35 castor oil, and/or Cremophor EL), polysorbates (e.g., polysorbate 20 and/or polysorbate 80), sorbitan monooleate, hydroxypropyl-beta-cyclodextrin (HPCD), polyoxyl 40 hydrogenated castor oil (i.e., Cremophor RH 40), polyoxyl hydroxystearates (e.g., Solutol HS 15), and combinations thereof.

In some embodiments, the compositions of the present disclosure may be co-administered to a subject with additional materials, such as other active agents and/or inactive ingredients. In some embodiments, the administered compositions may be utilized to treat and/or prevent disorders in a subject. In some embodiments, the disorders include, without limitation, prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steato-hepatitis (NASH), liver dysfunction characterized by fatty liver and/or insulin resistance, polycystic ovary syndrome, or combinations thereof. As such, in some embodiments, the present disclosure pertains to methods of treating or preventing one or more of the aforementioned disorders in a subject by administering the compositions of the present disclosure to the subject.

Administration of Compositions to Subjects

The compositions of the present disclosure may be administered to a subject in order to treat or prevent various disorders in the subject. In some embodiments, the disorders can be, but are not limited to, prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steato-hepatitis (NASH), liver dysfunction characterized by fatty liver and/or insulin resistance, polycystic ovary syndrome, or combinations thereof.

Various methods may be utilized to administer the compositions of the present disclosure to a subject. For instance, in some embodiments, the administration occurs by a method that includes, without limitation, oral administration, inhalation, subcutaneous administration, intravenous administration, intra-nasal administration, intra-dermal administration, trans-dermal administration, intraperitoneal administration, intramuscular administration, intrathecal injection, topical administration, central administration, peripheral administration, and combinations thereof. In some embodiments, the administering can be performed orally, intramuscularly, intranasally, subcutaneously, intra- or trans-dermally, intravenously, or combinations thereof.

In some embodiments, the compositions of the present disclosure can be administered to the subject via delivery agents. In some embodiments, the delivery agents can include various types of particles and/or targeting agents associated with the compositions of the present disclosure. For instance, in some embodiments, the delivery agents can be particles associated with the compositions of the present disclosure.

The particles associated with the compositions of the present disclosure may have various sizes. For instance, in some embodiments, the particles associated with the compositions of the present disclosure are in the form of nanoparticles. In some embodiments, the nanoparticles have diameters ranging from about 50 nm to about 500 nm. In some embodiments, the nanoparticles have diameters of about 100 nm to about 150 nm. In some embodiments, the nanoparticles can be, for example, polymeric nanoparticles, lipid-based nanoparticles, single wall or multiwall carbon nanotubes, fullerenes, and combinations thereof.

Targeting agents may be associated with the compositions of the present disclosure in various manners. For instance, in some embodiments, the targeting agents associated with the compositions of the present disclosure may be on a surface of a particle. In some embodiments, the targeting agents associated with the compositions of the present disclosure may be covalently linked to the surface of the particle. In some embodiments, the targeting agents associated with the compositions of the present disclosure may be linked to the surface of the particle through a linker, such as polyethylene glycol (PEG).

In some embodiments, the compositions of the present disclosure include a solubilizing agent. Solubilizing agents generally refer to one or more compounds that are capable of facilitating the solubilization of the compositions of the present disclosure in liquid formulations. Solubilizing agents may also be referred to as co-solvents or carriers.

In some embodiments, the solubilizing agents of the present disclosure include water miscible organic solvents. In some embodiments, the solubilizing agents of the present disclosure include, without limitation, polyethylene glycol (e.g., PEG 400 and/or PEG 300), glycerin, propylene glycol, ethanol, sorbitol, polyoxyethylated glycerides (e.g., Labrafil M-2125CS), polyoxyethylated oleic glycerides (e.g., Labrafil M-1944CS, Polyoxyl 35 castor oil, and/or Cremophor EL), polysorbates (e.g., polysorbate 20 and/or polysorbate 80), sorbitan monooleate, hydroxypropyl-beta-cyclodextrin (HPCD), polyoxyl 40 hydrogenated castor oil (i.e., Cremophor RH 40), polyoxyl hydroxystearates (e.g., Solutol HS 15), and combinations thereof.

Applications and Advantages

The present disclosure can have various advantages. For instance, in some embodiments, the compositions of the present disclosure can decrease glucose release or deposition of fat from the liver (leading to a cleaner liver), increase the uptake of glucose in fat and muscle cells (which lowers blood sugar levels), and cause lower levels of insulin. Furthermore, in some embodiments, the compositions of the present disclosure can increase cellular glucose uptake independently of proximal insulin signaling pathways, through increasing the pAkt/Akt ratio.

Moreover, since the compositions of the present disclosure are small molecule analogs of E4orf1, the compositions of the present disclosure do not have the same limitations as the E4orf1 protein (e.g., having no receptor for the protein in human cells). As evident from the cellular glucose uptake and pAKT/AKT data in the Examples, the compositions of the present disclosure successfully enter cells and produce the aforementioned results.

Furthermore, in some embodiments, the compositions of the present disclosure can modulate glucose uptake levels. In some embodiments, the compositions of the present disclosure can increase cellular glucose uptake. In some embodiments, the aforementioned compositions increase cellular glucose uptake in fat cells, muscle cells, or liver cells. In some embodiments, the aforementioned compositions increase cellular glucose uptake independently of proximal insulin signaling pathways. In some embodiments, the aforementioned compositions mimic function of E4orf1. In some embodiments, the aforementioned compositions mimic function of E4orf1 in glucose uptake and insulin signaling in cells. In some embodiments, the aforementioned compositions cause an increase in pAkt/Akt in cells.

In some embodiments, the compositions of the present disclosure can reduce endogenous insulin levels in the blood. In some embodiments, the compositions of the present disclosure improve blood glucose levels by reducing high levels of glucose in the blood, or reducing the rise in glucose levels or the duration of glucose elevation expected after eating food. In some embodiments, the compositions of the present disclosure reduce glucose output from the liver. In some embodiments, the compositions of the present disclosure prevent an increase in blood insulin levels, reduce production and secretion of insulin while improving blood glucose levels, and thereby prevent damage to pancreatic cells that make insulin. In some embodiments, the compositions of the present disclosure reduce fat accumulation in the liver. In some embodiments, the compositions of the present disclosure prevent accumulation of fat in the liver or reduce accumulated lipid from the liver.

As such, the methods and compositions of the present disclosure can be utilized to treat or prevent various diseases and conditions, including, without limitation, prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steato-hepatitis (NASH), liver dysfunction characterized by fatty liver and/or insulin resistance, polycystic ovary syndrome, or combinations thereof. More specifically, the methods and compositions of the present disclosure can be utilized as anti-diabetic agents to treat or prevent diabetes.

ADDITIONAL EMBODIMENTS

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Anti-Diabetic Property of Small Molecule Analogs of E4orf1 Protein E4orf1 protein of human adenovirus 36 is necessary and sufficient to improve glycemic control through increased glucose uptake in adipose tissue and muscle cells and by reducing glucose output from the liver. E4orf1 bypasses the proximal insulin signaling pathway and uses distal insulin signaling pathway to uptake glucose. E4orf1 activates Ras which in turn activates PI3K to phosphorylate Akt and promotes the translocation of glucose transporter Glut4 to the membrane for glucose uptake. While many antidiabetic drugs are dependent on the proximal insulin signaling pathway, E4orf1 can uptake glucose independent of the proximal insulin signaling pathway. Hence, E4orf1 can be used as a potential drug to treat diabetes more effectively.

However, human cells lack receptors for the E4orf1 protein. Accordingly, Applicants developed chemical analogs of E4orf1, termed BT324, BT325, BT326, BT327, BT328, and BT329. These analogs were tested in vitro to check if they mimic the function/action of E4orf1 on glucose uptake and insulin signaling.

As disclosed herein, of the six E4orf1 analogs tested, four analogs, BT324, BT325, BT327, and BT329 significantly increase glucose uptake repeatedly. Described and illustrated in further detail herein are the six analogs and the results from testing them on 3T3L1 preadipocytes with DMSO and insulin used as controls.

Example 1.1. Methods

The following E4orf1 analogs, as shown in FIG. 1 and described below in Table 1, were developed and synthesized.

TABLE 1

| Compounds | Molecular Weight |
|---|---|
| BT324 | 238.62 |
| BT325 | 224.60 |
| BT326 | 237.64 |
| BT327 | 223.61 |
| BT328 | 245.08 |
| BT329 | 160.18 |

Example 1.2. Dissolving Analogs in DMSO to Treat Cells

All analogs were dissolved in 2 ml of DMSO in dark (to prevent exposure to light). They were aliquoted (200 µl) to avoid repeated freeze and thaw and stored at 4° C.

Example 1.3. Experiments—Glucose Uptake and Western Blot

3T3L1 preadipocytes (passage number 8 below) were used to treat with analogs. As control, cells were treated with equal volumes of DMSO. As positive control, cells were treated with 100 nM insulin. Cells at 70% confluency were treated with analogs (2 μl/ml of media) in dark for 24 hr. Post 24 hr treatment, cells were used either to determine glucose uptake or to obtain cell lysates for determining pAKT abundance by Western blot analysis.

Example 1.4. Results

Figure 3:
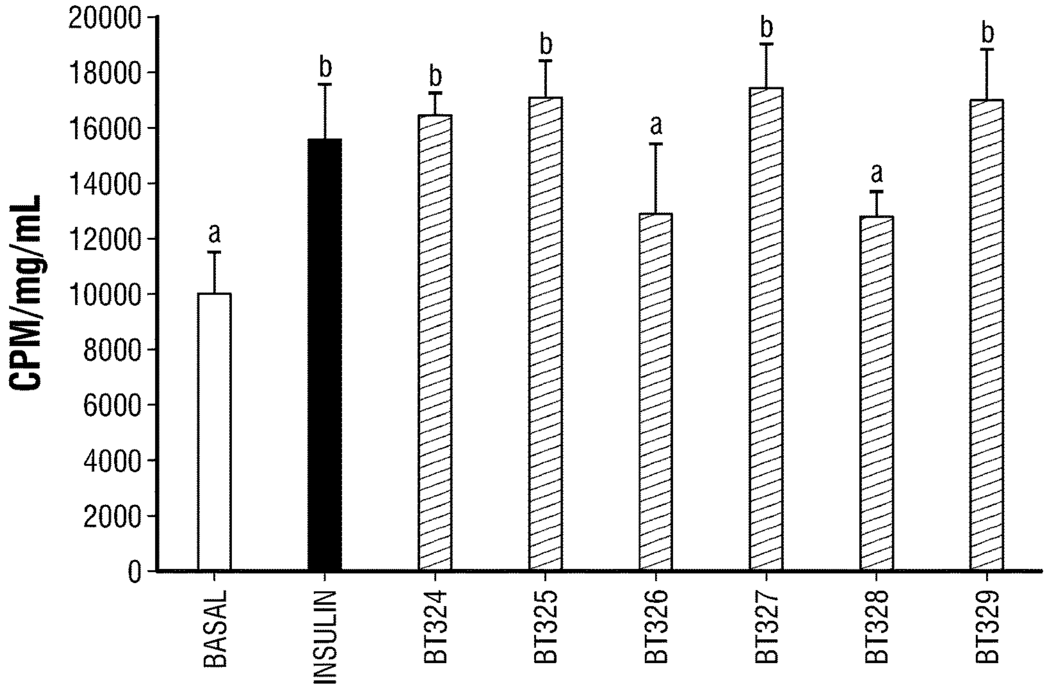
FIG. 3 illustrates that selected E4orf1 chemical analogs increase glucose uptake. 3T3L1 preadipocytes were treated with dimethyl sulfoxide (DMSO) or insulin or treated with analogs BT324, BT325, BT326, BT327, BT328, and BT329. The treatments were compared using one way analysis of variance (ANOVA) and post hoc Tukey's test. Groups sharing same letters are not statistically significant.
Figure 4:
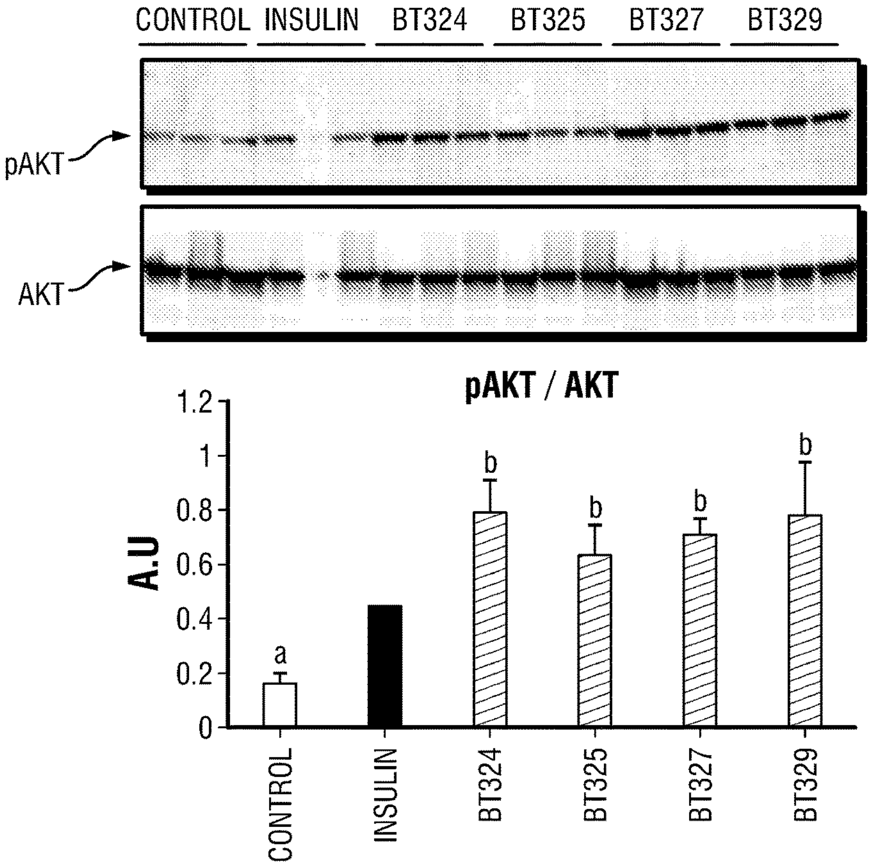
FIG. 4 illustrates that the E4orf1 chemical analogs that increase glucose uptake also increase pAkt levels—the underlying mechanism for increasing cellular glucose uptake. 3T3L1 preadipocytes were treated with DMSO or insulin or with analogs BT324, BT325, BT327, or BT329. Post 24 hr incubation in the dark, cell lysates were collected and 20 μg of protein was loaded and probed for pAkt/Akt. Band intensities were analyzed using Image J software. Groups sharing same letters are not statistically significant.

Of the six E4orf1 analogs tested, four analogs, BT324, BT325, BT327 and BT329 significantly increased glucose uptake repeatedly (individual experiments repeated 3 times), as shown in FIG. 3. Cell signaling Western blot data showed significant increase in pAkt/Akt for the four analogs, as shown in FIG. 4.

Example 1.5. Conclusion

E4orf1 analogs BT324, BT325, BT327, and BT329 increase cellular glucose uptake and enhance insulin signaling protein, similar to that by E4orf1. These analogs are good candidates as anti-diabetic agents to treat or prevent diabetes.

Example 2. Small Molecule Candidates

This Example describes developing small molecule candidates that mimic the action of E4orf1.

Example 2.1. Development of Small Molecules

While E4orf1 can improve glycemic control, delivering this exogenous protein to cells is challenging. To address this challenge, Applicants considered a peptidomimetic approach, which has shown to improve safety and minimize proteolytic susceptibility. Applicants successfully addressed this challenge by developing small molecule candidates that mimic the action of E4orf1. This will provide information to take the lead molecules towards clinical studies.

The exact crystal structure of the E4orf1 is not known. Hence, Applicants employed the DNA and amino acid sequence of E4orf1 protein to construct homology modeling using Applicants' newly developed software. In this process, Applicants took base pairs of DNA and used European Bioinformatics Institute (EMBL-EBI) database search for the types of amino acid sequence that could be aligned with the existing proteins. Ad36 E4orf1 Protein translation sequence is:

```
                                      (SEQ ID NO: 1)
MAESLYAFIDSPGGIAPVQEGASNRYIFFCPESFHIPPHGVILLHLRVS

VLVPTGYQGRFMALNDYHARGILTQSDVIFAGRRHDLSVLLFNHTDRFL

YVREGHPVGTLLLERVIFPSVRIATLV
```

After determining the protein sequence, Applicants refined using Molsoft ICM and Molecular Operating Environment and remodeled the active site and generated the active site of the protein in silico as previously described. Next, Applicants screened their small libraries of chemical compounds, which are theoretical molecules. After identifying the hits in-silico, Applicants synthesized the molecules based on new reactions developed by Applicants.

Figure 5:
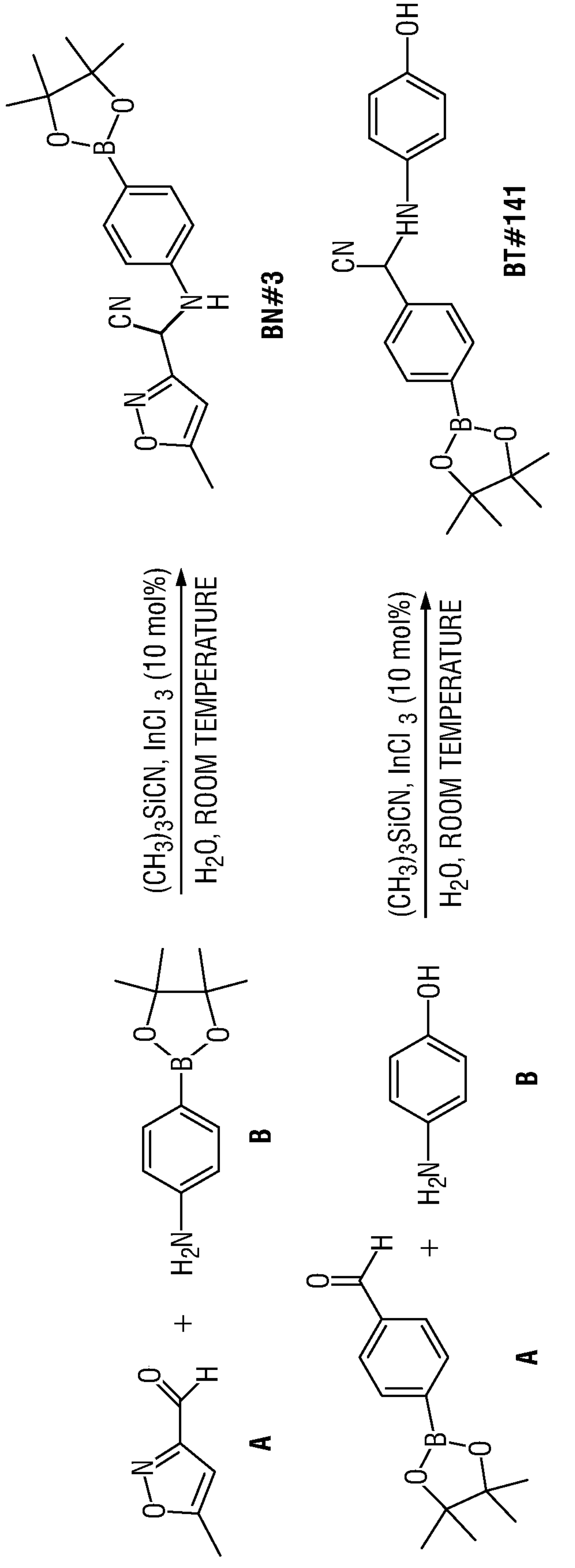
FIG. 5 illustrates synthesis of lead molecules BN #3 and BT #141.

Amino nitriles based pharmacophore groups are well accepted in drug discovery. All compounds Applicant synthesized contain alpha-aminonitrile pharmacophore groups and all derivatives are substituted with amino groups containing boronic acids (FIG. 5). Hence, the alpha-aminonitrile containing boronic acid derivatives are new compounds. These molecules were characterized using routine analytical tools used in medicinal chemistry, such as Nuclear Magnetic Resonance (NMR), both 1H proton and 13Carbon NMR, and High Resolution Mass Spectroscopy (HRMS). The purity of the compounds was determined by High Performance Liquid Chromatography (HPLC).

The compounds were found to be stable, white solid, not pyrophoric, and not water reactive. The compounds were also found to be water soluble, and with a log P value under the therapeutic index (3.5-4.5).

Applicants' lab has the capacity to develop clinical grade compounds needed (BN #3 and BT #141). The general procedure to synthesize these amino nitriles is as follows (FIG. 5). To a 10 mL round bottomed flask containing aldehyde A (0.5 mmol, 1.0 eq), amine B (0.5 mmol, 1.0 eq), Trimethylsilyl cyanide (TMSCN; 0.6 mmol, 1.2 eq) and water (2 mL), $InCl_3$ (Indium Chloride; 0.05 mmol, 10 mol %) is added as the catalyst. The resulting mixture is stirred overnight at room temperature. After the reaction is complete, the crude solid product is filtered and washed by water and hexane, and further purified by silica gel chromatography using ethylacetate and hexanes as solvent. All compounds are characterized by using proton, Carbon NMR and HRMS.

Example 2.2. In Vitro Screening of Small Molecules

To determine optimal dose and toxicity, 3T3-L1 preadipocytes were exposed to different concentrations (5 μM, 10 μM, 20 μM, 50 μM and 100 μM) of 5 different small molecules in dimethyl sulfoxide (DMSO). Control cells were exposed to DMSO alone. Concentrations of 50 μM and 100 μM showed extreme toxicity and cell death after day 2 of exposure, while exposure to other concentrations was followed until day 5 and based on percent cell survival, 20 μM concentration was determined to be optimal for testing glucose disposal with these compounds.

Figure 6:
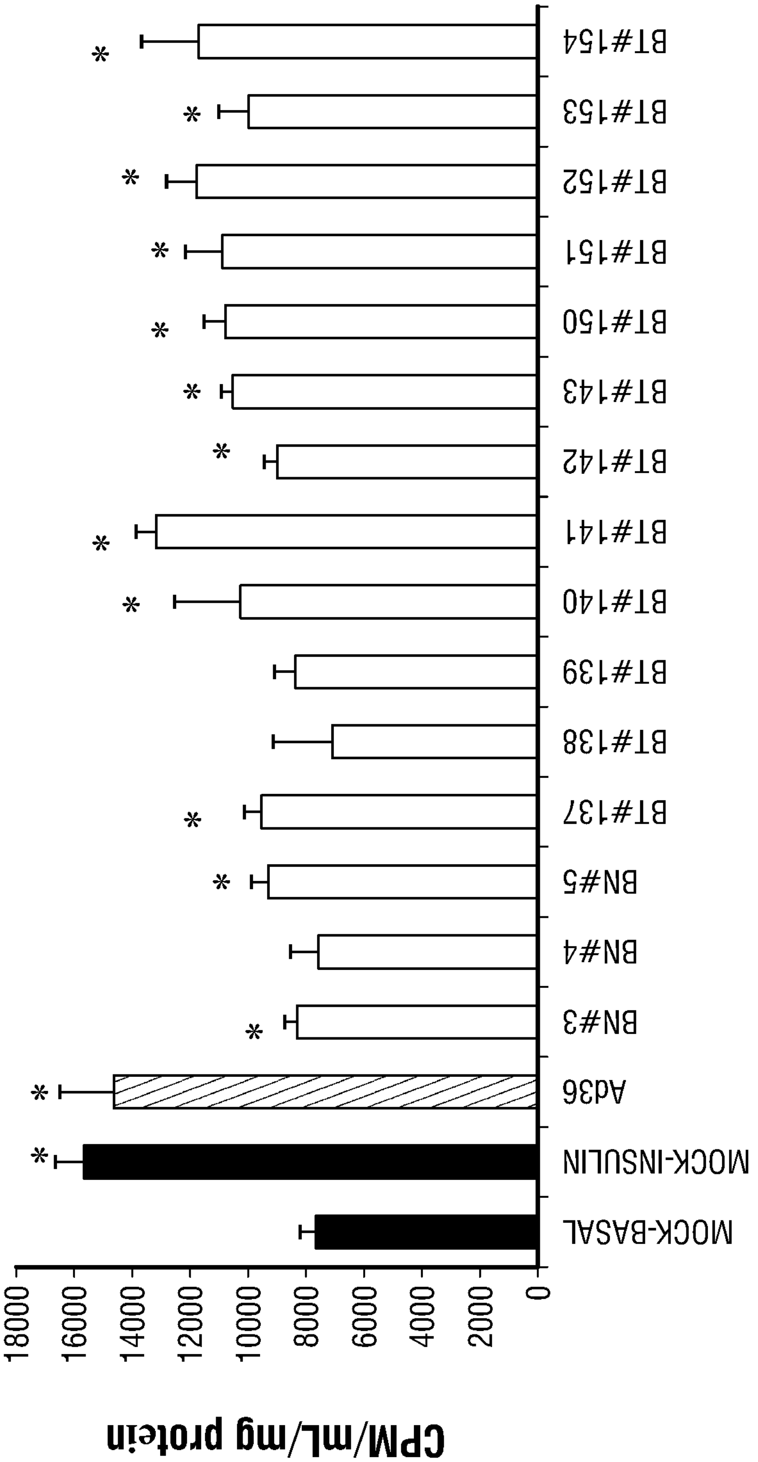
FIG. 6 illustrates screening of small molecules for potential to increase cellular glucose uptake.

Next, over time, Applicants tested cellular glucose uptake with 41 different E4orf1 analog small molecules in 3T3-L1 pre-adipocytes, mature adipocytes and murine skeletal muscle cells. Cells were exposed to 20 μM/well of E4orf1 analogs. Glucose uptake by cells was determined 24 h later. Insulin and human adenovirus Ad36 were used as positive controls for glucose uptake. Data from a batch of 15 compounds screened are presented in FIG. 6. The * indicates statistical significance after Bonferroni correction for multiple comparisons. Data on cell signaling including Ras, pAKT, Glut4 for selected compounds are not presented due to space constrains, as this PAR does not focus on mechanism of action.

Applicants conducted glucose uptake assays for compounds several separate times. BN #3 and BT #141 had about 70% greater glucose uptake compared to control in other replications not presented herein.

Example 2.3. Candidate and Lead Molecule Identification

Of the 41 different small molecules tested, Applicants selected 12 candidate compounds, 4 aminonitrile (BN #3, BN #5, BT #141, BT #143) and 8 chromene (BT #156, BT #158, BT #166, BT #170, BT #181, BT #185, BT #186 and BT #188) that displayed consistently significant increase in cellular glucose when tested 3 or more times in different cell types. From the 12 candidate compounds Applicants tested 4 molecules (BN #3, BT #141, BT #143 and BT #181) in vivo.

Example 2.4. Improvement of Glucose Disposal by Lead Molecules

Figure 7:
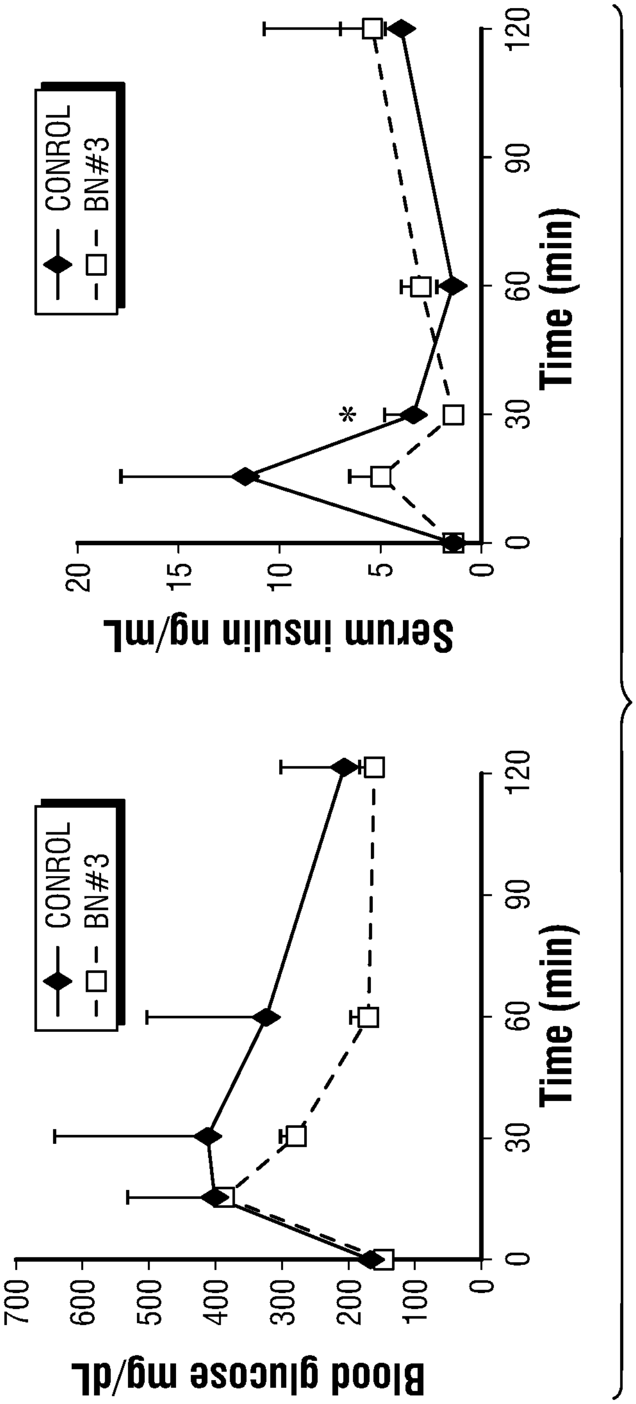
FIG. 7 illustrates improved glucose disposal and lower insulin secretion in BN #3 treated mice (mean±standard deviation).
Figure 8:
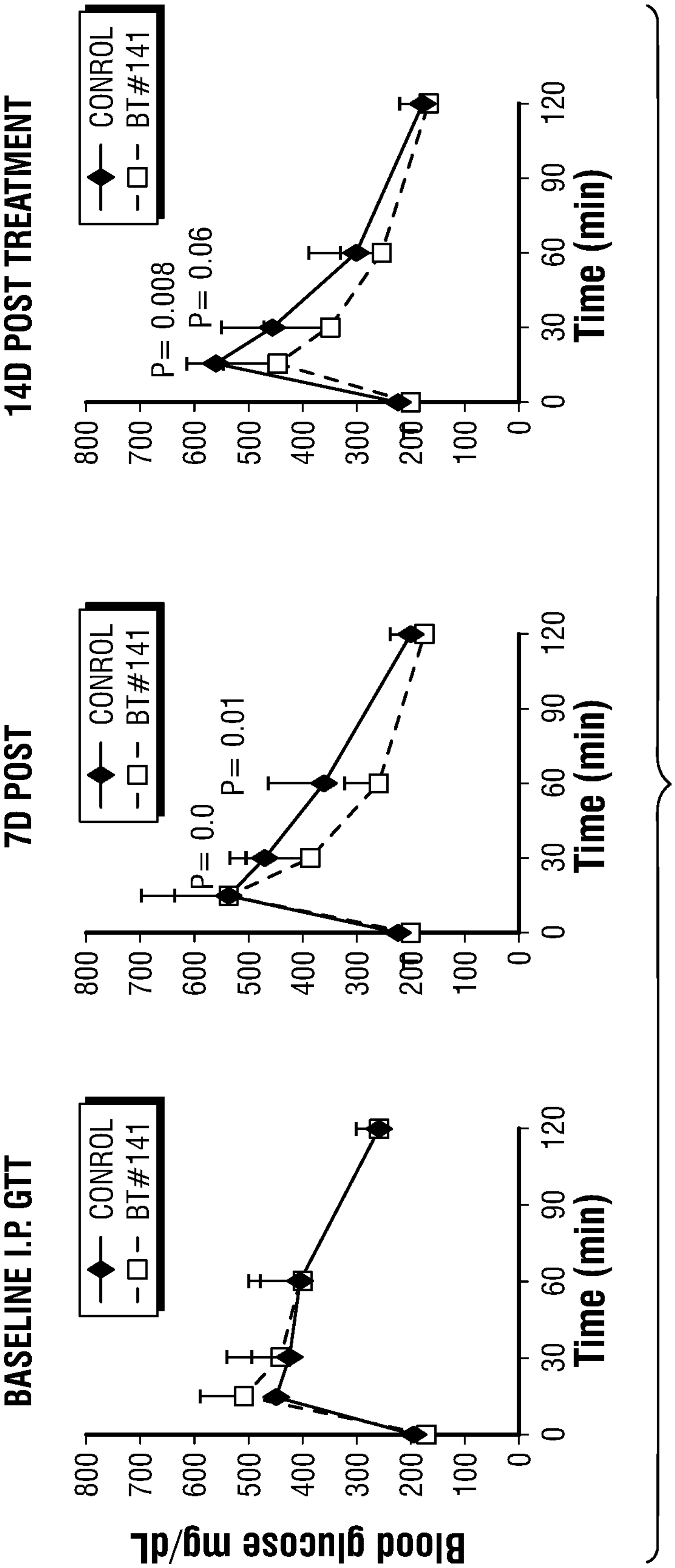
FIG. 8 illustrates improved glucose disposal in BN #141 treated mice (mean±standard deviation).

To determine improvement in glucose disposal in vivo, 10 wk old C57BL/6J male mice (Jax Laboratories) on a 60% kcal high-fat diet (Research diets, Inc.) since 6 weeks of age were divided into weight-matched groups. In individual experiments, mice were treated with daily injection of 4 mg/kg of respective small molecules (BN #3, BT #141, BT #143 and BT #181) or DMSO alone as control. Improvement in glycemic control was determined by glucose tolerance test (GTT) performed at baseline (prior to treatment), 7 days and/or 14 days post-treatment. Insulin-independent action of the small molecules was also measured by collecting blood during GTT and quantifying serum insulin by enzyme-linked immunosorbent assay (ELISA). Candidate compounds BT #143 and BT #181 did not show any significant improvement in glucose clearance compared to control (DMSO) mice (data not shown). However, BN #3 and BT #141 showed improved glycemic control compared with control mice, respectively (FIG. 7 and FIG. 8).

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of treating or preventing a disorder in a subject, wherein the method comprises:

administering a composition to the subject, wherein the composition comprises a compound selected from the group consisting of:

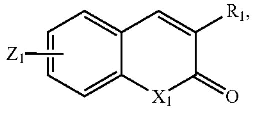,

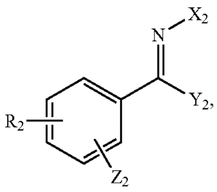, or combinations thereof, wherein $R_1$ is selected from the group consisting of $COOCH_3$ or COOH, wherein $R_2$ is selected from the group consisting of $OCH_3$ or ethynyl (CCH), wherein $X_1$ is selected from the group consisting of O or NH, wherein $X_2$ is OH, wherein $Z_1$ is Cl, wherein $Z_2$ is selected from the group consisting of Br or hydrogen, and wherein $Y_2$ is $NH_2$;

wherein the disorder to be treated is prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steatohepatitis (NASH), liver dysfunction characterized by fatty liver and/or insulin resistance, polycystic ovary syndrome, or combinations thereof, and wherein the disorder to be prevented is prediabetes, diabetes type 2, insulin resistance, hyperinsulinemia, hyperglycemia, metabolic syndrome, hepatic steatosis, non-alcoholic fatty liver disease (NAFLD), non-alcoholic steatohepatitis (NASH), liver dysfunction characterized by fatty liver and/or insulin resistance, or combinations thereof.

2. A method of treating or preventing a disorder in a subject, wherein the method comprises:

administering a composition to the subject, wherein the composition comprises a compound selected from the group consisting of:

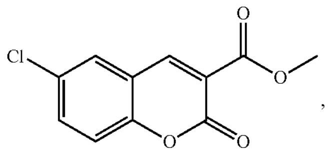 [SMILES: COC(=O)c1cc2cc(Cl)ccc2oc1=O]
,

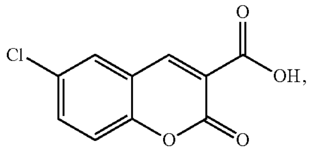

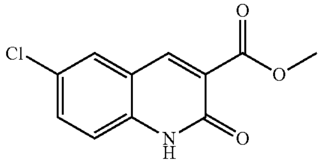
,

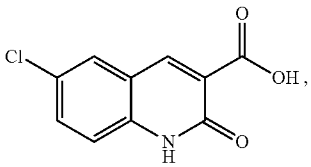
,

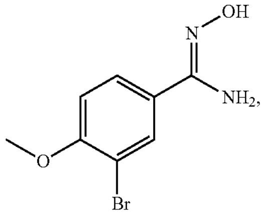

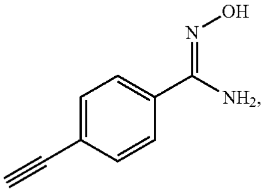

or combinations thereof;

wherein the disorder to be treated is prediabetes, diabetes type 1, diabetes type 2, insulin resistance, hyperinsulinemia, hyperglycemia, metabolic syndrome, hepatic steatosis, non-alcoholic fatty liver disease (NAFLD), non-alcoholic steatohepatitis (NASH), liver dysfunction characterized by fatty liver and/or insulin resistance, polycystic ovary syndrome, or combinations thereof, and wherein the disorder to be prevented is prediabetes, diabetes type 2, insulin resistance, hyperinsulinemia, hyperglycemia, metabolic syndrome, hepatic steatosis, non-alcoholic fatty liver disease (NAFLD), non-alcoholic steatohepatitis (NASH), liver dysfunction characterized by fatty liver and/or insulin resistance, or combinations thereof.

3. The method of claim 1 or 2, wherein the administering is performed orally, intramuscularly, intranasally, subcutaneously, intra- or trans-dermally, intravenously, or combinations thereof.

4. The method of claim 1 or 2, wherein the composition reduces endogenous insulin levels in the blood; mimics function of early 4 open reading frame 1 protein of human adenovirus 36 (E4orf1); causes an increase in pAkt/Akt ratios; improves blood glucose levels by reducing high levels of glucose in the blood, or reducing the rise in glucose levels or the duration of glucose elevation expected after eating food, or reducing glucose output from the liver; prevents an increase in blood insulin levels; reduces production and secretion of insulin while improving blood glucose levels, thereby preventing damage to pancreatic cells that make insulin; reduces fat accumulation in the liver or reduce accumulated lipid from the liver; prevents accumulation of fat in the liver; modulates cellular glucose uptake levels; increases cellular glucose uptake levels; increases cellular glucose uptake independently of proximal insulin signaling pathways; or combinations thereof.

5. The method of claim 2, wherein the composition comprises:

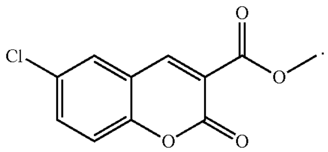

6. The method of claim 2, wherein the composition comprises:

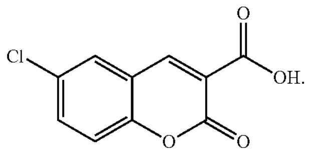 [SMILES: O=C(O)c1cc2cc(Cl)ccc2oc1=O]

7. The method of claim 2, wherein the composition comprises:
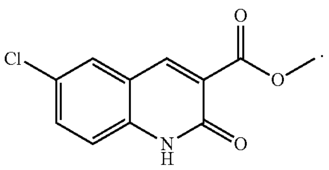 [SMILES: COC(=O)c1cc2cc(Cl)ccc2[nH]c1=O]
8. The method of claim 2, wherein the composition comprises:
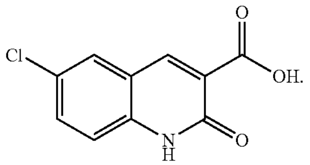 [SMILES: O=C(O)c1cc2cc(Cl)ccc2[nH]c1=O]
9. The method of claim 2, wherein the composition comprises:
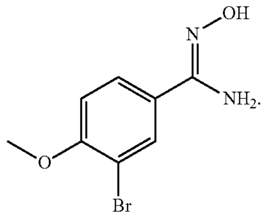
10. The method of claim 2, wherein the composition comprises:
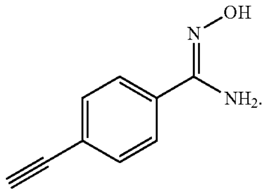
* * * * *